United States Patent
Adler

(10) Patent No.: US 7,451,765 B2
(45) Date of Patent: Nov. 18, 2008

(54) INTRA-BRONCHIAL APPARATUS FOR ASPIRATION AND INSUFFLATION OF LUNG REGIONS DISTAL TO PLACEMENT OR CROSS COMMUNICATION AND DEPLOYMENT AND PLACEMENT SYSTEM THEREFOR

(76) Inventor: Mark Adler, 12720 Coachman Ct., Poway, CA (US) 92064

( * ) Notice: Subject to any disclaimer, the term of this patent is extended or adjusted under 35 U.S.C. 154(b) by 74 days.

(21) Appl. No.: 11/174,235

(22) Filed: Jul. 1, 2005

(65) Prior Publication Data

US 2006/0102186 A1     May 18, 2006

Related U.S. Application Data

(60) Provisional application No. 60/629,451, filed on Nov. 18, 2004.

(51) Int. Cl.
*A61M 16/00* (2006.01)
*A62B 9/06* (2006.01)

(52) U.S. Cl. .................. 128/207.14; 128/200.26; 128/207.15; 128/207.16; 606/108; 604/528; 623/1.11; 623/1.2

(58) Field of Classification Search ............ 128/200.26, 128/207.14, 207.15, 207.16; 604/528; 623/1.11, 623/1.2, 23.64, 23.65, 1.24–1.26, 2.1–2.15; 606/108
See application file for complete search history.

(56) References Cited

U.S. PATENT DOCUMENTS

| | | | | | |
|---|---|---|---|---|---|
| 2,127,215 | A | * | 8/1938 | Gwathmey | 128/207.14 |
| 2,541,691 | A | * | 2/1951 | Eicher | 27/24.2 |
| 3,169,529 | A | * | 2/1965 | Koenig | 128/207.14 |
| 3,330,271 | A | * | 7/1967 | Hozier | 128/205.29 |
| 3,540,431 | A | * | 11/1970 | Mobin-Uddin | 128/899 |
| 3,565,079 | A | * | 2/1971 | Jackson | 128/207.15 |
| 3,616,799 | A | * | 11/1971 | Sparks | 128/207.15 |
| 3,671,979 | A | * | 6/1972 | Moulopoulos | 623/2.11 |
| 4,007,743 | A | * | 2/1977 | Blake | 606/232 |
| 4,198,970 | A | * | 4/1980 | Luomanen | 128/207.15 |
| 4,270,531 | A | * | 6/1981 | Blachly et al. | 128/207.14 |
| 4,315,505 | A | * | 2/1982 | Crandall et al. | 128/200.26 |
| 4,363,320 | A | * | 12/1982 | Kossove | 128/207.14 |
| 4,502,478 | A | * | 3/1985 | Lifton | 128/862 |
| 4,505,414 | A | * | 3/1985 | Filipi | 227/19 |
| 4,588,395 | A | * | 5/1986 | Lemelson | 604/59 |
| 4,595,005 | A | * | 6/1986 | Jinotti | 128/205.24 |
| 4,601,465 | A | * | 7/1986 | Roy | 482/13 |
| 4,649,913 | A | * | 3/1987 | Watson | 128/207.14 |
| 4,662,885 | A | * | 5/1987 | DiPisa, Jr. | 623/23.68 |
| 4,691,702 | A | * | 9/1987 | Chantzis | 128/207.16 |
| 4,727,872 | A | * | 3/1988 | Hawk | 128/207.14 |
| 4,942,873 | A | * | 7/1990 | Irwin et al. | 128/203.11 |
| 4,966,141 | A | * | 10/1990 | Bacaner et al. | 128/207.14 |
| 5,042,473 | A | * | 8/1991 | Lewis | 128/205.24 |

(Continued)

*Primary Examiner*—Kevin C. Sirmons
*Assistant Examiner*—Nihir Patel
(74) *Attorney, Agent, or Firm*—Craig M. Stainbrook; Stainbrook & Stainbrook, LLP

(57) ABSTRACT

An anchored intra-bronchial apparatus for placement and deployment into selected airways and a method for using the same. When deployed, the apparatus creates a restriction of air flow to one or more targeted lung regions and achieves total lung volume reduction through a collapse or partial collapse of the targeted regions. The air flow valve of the apparatus includes a through lumen that permits drug delivery concurrent with lung volume reduction procedure.

4 Claims, 15 Drawing Sheets

U.S. PATENT DOCUMENTS

| | | | | |
|---|---|---|---|---|
| 5,056,515 A | * | 10/1991 | Abel | 128/207.15 |
| 5,065,757 A | * | 11/1991 | Dragisic et al. | 128/207.14 |
| 5,103,817 A | * | 4/1992 | Reisdorf et al. | 128/207.15 |
| 5,152,283 A | * | 10/1992 | Yamasaki | 128/202.28 |
| 5,234,447 A | * | 8/1993 | Kaster et al. | 606/153 |
| 5,251,616 A | * | 10/1993 | Desch | 128/200.26 |
| 5,275,605 A | * | 1/1994 | Winkler | 606/128 |
| 5,279,548 A | * | 1/1994 | Essig et al. | 604/27 |
| 5,290,295 A | * | 3/1994 | Querals et al. | 623/1.23 |
| 5,361,754 A | * | 11/1994 | Stuart | 128/207.17 |
| 5,456,720 A | * | 10/1995 | Schultz et al. | 623/23.64 |
| 5,458,139 A | * | 10/1995 | Pearl | 128/207.14 |
| 5,462,049 A | * | 10/1995 | Yavitz | 128/205.27 |
| 5,487,381 A | * | 1/1996 | Jinotti | 128/207.14 |
| 5,571,114 A | * | 11/1996 | Devanaboyina | 606/108 |
| 5,582,166 A | * | 12/1996 | Lee | 128/207.14 |
| 5,620,408 A | * | 4/1997 | Vennes et al. | 600/114 |
| 5,642,730 A | * | 7/1997 | Baran | 128/207.14 |
| 5,653,229 A | * | 8/1997 | Greenberg | 128/207.15 |
| 5,655,528 A | * | 8/1997 | Pagan | 128/207.14 |
| 5,676,132 A | * | 10/1997 | Tillotson et al. | 128/204.23 |
| 5,694,929 A | * | 12/1997 | Christopher | 128/207.14 |
| 5,697,365 A | * | 12/1997 | Pell | 128/207.15 |
| 5,713,348 A | * | 2/1998 | Pell | 128/202.27 |
| 5,715,815 A | * | 2/1998 | Lorenzen et al. | 128/207.14 |
| 5,765,557 A | * | 6/1998 | Warters | 128/207.14 |
| 5,813,402 A | * | 9/1998 | Jinotti | 128/207.16 |
| 5,819,727 A | * | 10/1998 | Linder | 128/200.26 |
| 5,819,733 A | * | 10/1998 | Bertram | 128/207.15 |
| 5,824,064 A | * | 10/1998 | Taheri | 128/898 |
| 5,830,217 A | * | 11/1998 | Ryan | 623/1.11 |
| 5,840,081 A | * | 11/1998 | Andersen et al. | 623/1.11 |
| 5,964,217 A | * | 10/1999 | Christopher | 128/200.26 |
| 6,119,695 A | * | 9/2000 | Augustine et al. | 128/207.15 |
| 6,152,931 A | * | 11/2000 | Nadal et al. | 606/108 |
| 6,216,696 B1 | * | 4/2001 | van den Berg | 128/207.14 |
| 6,258,100 B1 | | 7/2001 | Alferness et al. | |
| 6,293,951 B1 | * | 9/2001 | Alferness et al. | 606/108 |
| 6,328,689 B1 | | 12/2001 | Gonzalez et al. | |
| 6,355,061 B1 | * | 3/2002 | Quiachon et al. | 623/1.36 |
| 6,371,108 B1 | * | 4/2002 | Christianson | 128/201.11 |
| 6,374,827 B1 | * | 4/2002 | Bowden et al. | 128/207.14 |
| 6,378,521 B1 | * | 4/2002 | Van Den Berg | 128/207.14 |
| 6,386,197 B1 | * | 5/2002 | Miller | 128/206.11 |
| 6,394,093 B1 | * | 5/2002 | Lethi | 128/207.18 |
| 6,398,758 B1 | * | 6/2002 | Jacobsen et al. | 604/104 |
| 6,425,902 B1 | * | 7/2002 | Love | 606/150 |
| 6,514,264 B1 | * | 2/2003 | Naglreiter | 606/151 |
| 6,527,780 B1 | * | 3/2003 | Wallace et al. | 606/108 |
| 6,558,429 B2 | * | 5/2003 | Taylor | 623/23.68 |
| 6,592,593 B1 | * | 7/2003 | Parodi et al. | 606/108 |
| 6,592,594 B2 | * | 7/2003 | Rimbaugh et al. | 606/108 |
| 6,599,311 B1 | * | 7/2003 | Biggs et al. | 606/232 |
| 6,623,490 B1 | * | 9/2003 | Crane et al. | 606/108 |
| 6,626,930 B1 | * | 9/2003 | Allen et al. | 606/213 |
| 6,632,243 B1 | * | 10/2003 | Zadno-Azizi et al. | 623/1.24 |
| 6,645,205 B2 | * | 11/2003 | Ginn | 606/41 |
| 6,655,382 B1 | * | 12/2003 | Kolobow | 128/204.25 |
| 6,679,264 B1 | * | 1/2004 | Deem et al. | 128/207.16 |
| 6,712,812 B2 | | 3/2004 | Roschak et al. | |
| 6,722,367 B1 | * | 4/2004 | Blom | 128/207.14 |
| 6,746,489 B2 | * | 6/2004 | Dua et al. | 623/23.68 |
| 6,752,828 B2 | * | 6/2004 | Thornton | 623/1.24 |
| 6,767,362 B2 | * | 7/2004 | Schreck | 623/2.11 |
| 6,802,316 B2 | * | 10/2004 | Fulgham | 128/207.14 |
| 6,814,077 B1 | * | 11/2004 | Eistert | 128/207.14 |
| 6,837,237 B2 | * | 1/2005 | Kirn | 128/200.24 |
| 6,840,242 B1 | * | 1/2005 | McCoy | 128/207.14 |
| 6,848,443 B2 | * | 2/2005 | Schmidt et al. | 128/200.23 |
| 6,895,966 B2 | * | 5/2005 | Christopher | 128/207.15 |
| 6,901,958 B2 | * | 6/2005 | Taylor | 137/614.2 |
| 6,905,518 B2 | * | 6/2005 | Ginn | 623/23.65 |
| 6,913,016 B2 | * | 7/2005 | Pietrantoni | 128/204.29 |
| 6,951,571 B1 | * | 10/2005 | Srivastava | 623/1.24 |
| 6,958,079 B1 | * | 10/2005 | Taylor et al. | 623/23.68 |
| 6,989,027 B2 | * | 1/2006 | Allen et al. | 623/2.18 |
| 6,994,711 B2 | * | 2/2006 | Hieshima et al. | 606/108 |
| 6,997,189 B2 | * | 2/2006 | Biggs et al. | 128/898 |
| 7,011,094 B2 | * | 3/2006 | Rapacki et al. | 128/207.15 |
| 7,013,890 B2 | * | 3/2006 | Wakabayashi | 128/200.26 |
| 7,033,387 B2 | * | 4/2006 | Zadno-Azizi et al. | 623/1.24 |
| 7,041,117 B2 | * | 5/2006 | Suon et al. | 606/200 |
| 7,081,131 B2 | * | 7/2006 | Thornton | 623/1.24 |
| 2001/0001957 A1 | * | 5/2001 | Allgeyer | 128/207.15 |
| 2003/0037789 A1 | * | 2/2003 | Klinberg et al. | 128/207.14 |
| 2003/0070682 A1 | | 4/2003 | Wilson et al. | |
| 2003/0181922 A1 | | 9/2003 | Alferness | |
| 2003/0195385 A1 | | 10/2003 | DeVore | |
| 2003/0216769 A1 | | 11/2003 | Dillard et al. | |
| 2004/0035432 A1 | * | 2/2004 | Gostelow | 128/207.29 |
| 2004/0143282 A1 | | 7/2004 | Dillard et al. | |
| 2004/0167636 A1 | | 8/2004 | Dillard et al. | |
| 2004/0206349 A1 | | 10/2004 | Alferness et al. | |
| 2004/0211412 A1 | | 10/2004 | Alferness et al. | |
| 2004/0243140 A1 | | 12/2004 | Alferness et al. | |
| 2005/0033310 A1 | | 2/2005 | Alferness et al. | |
| 2005/0033344 A1 | | 2/2005 | Dillard et al. | |
| 2005/0143809 A1 | * | 6/2005 | Salahieh et al. | 623/2.11 |

* cited by examiner

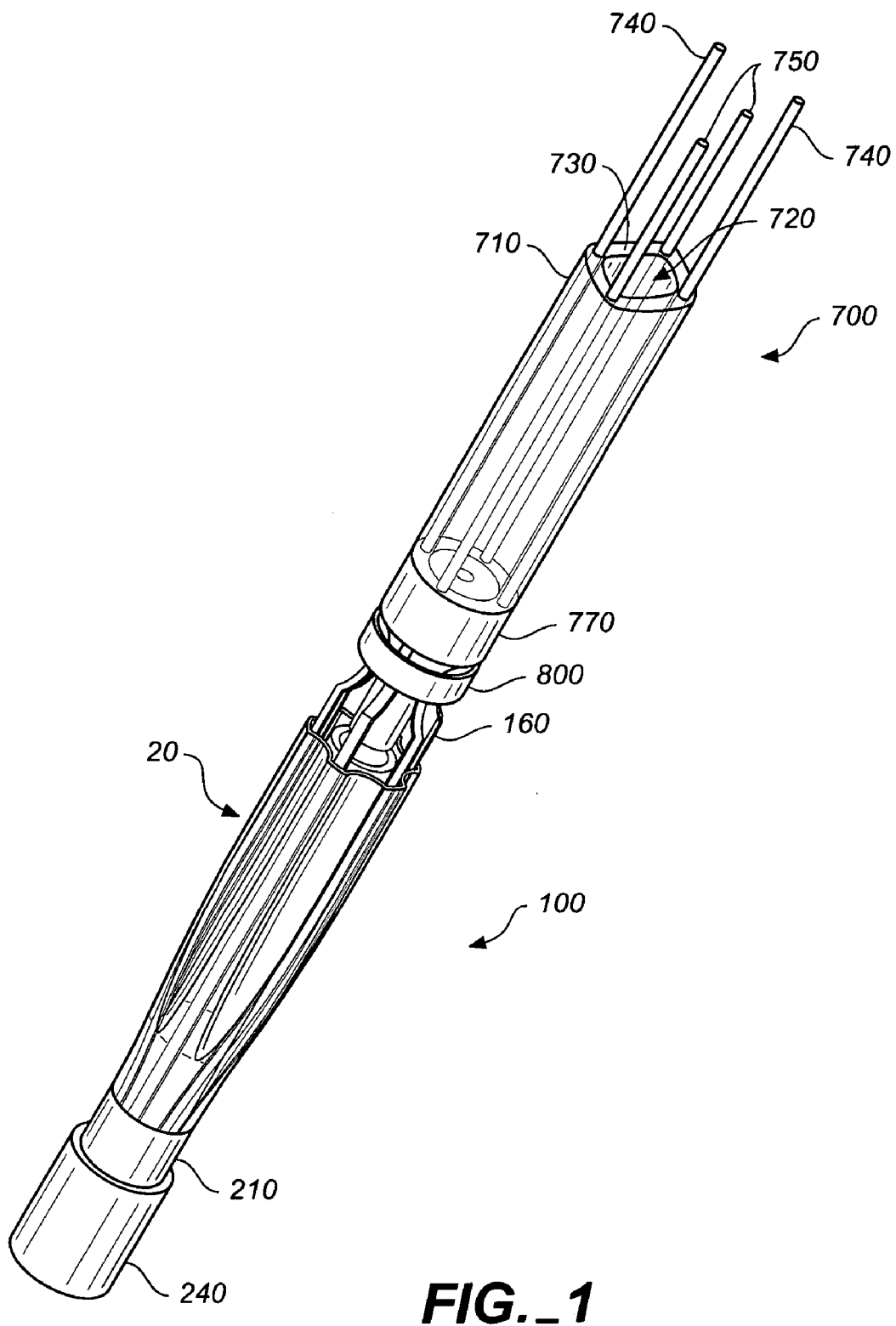
FIG._1

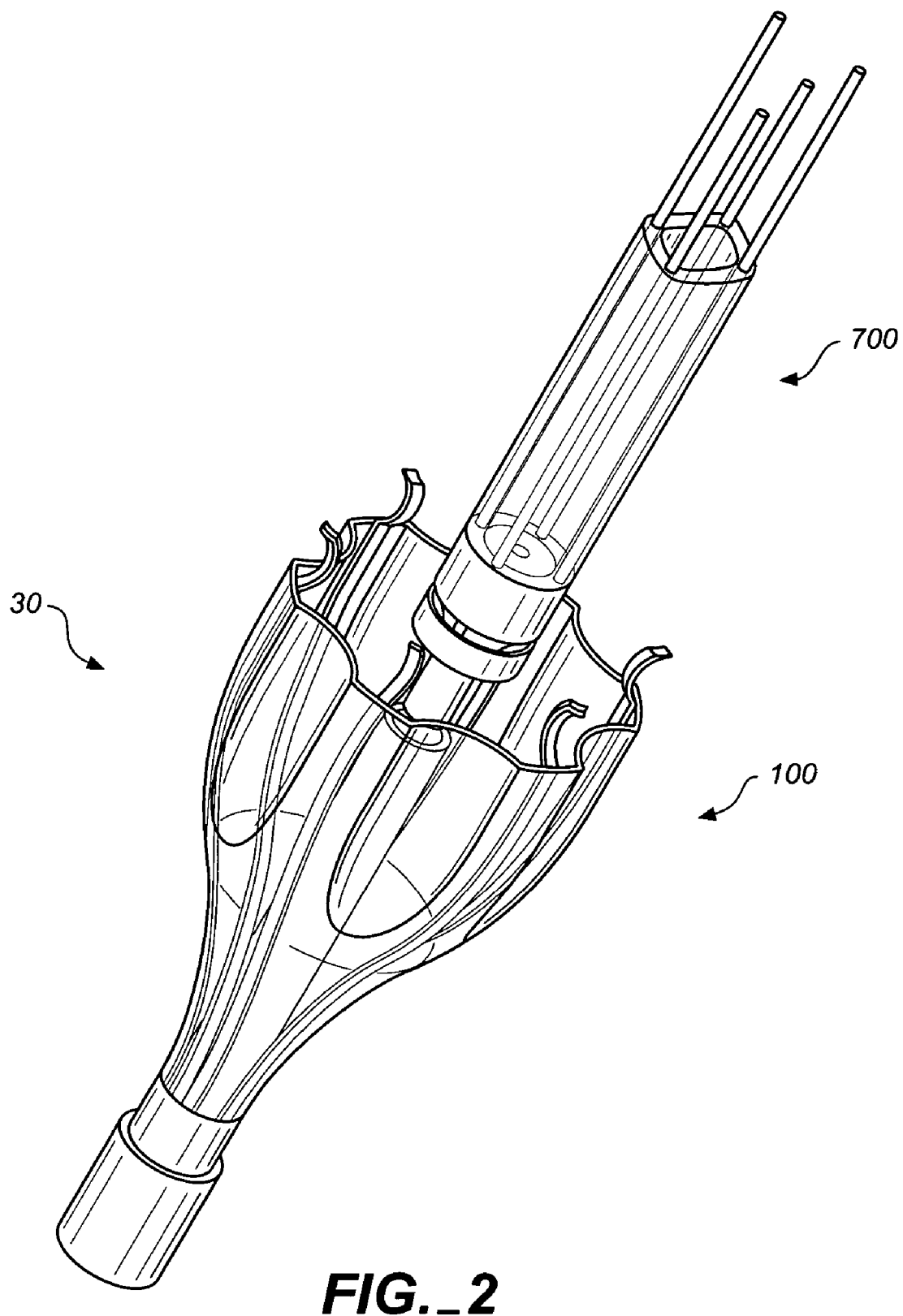
*FIG._2*

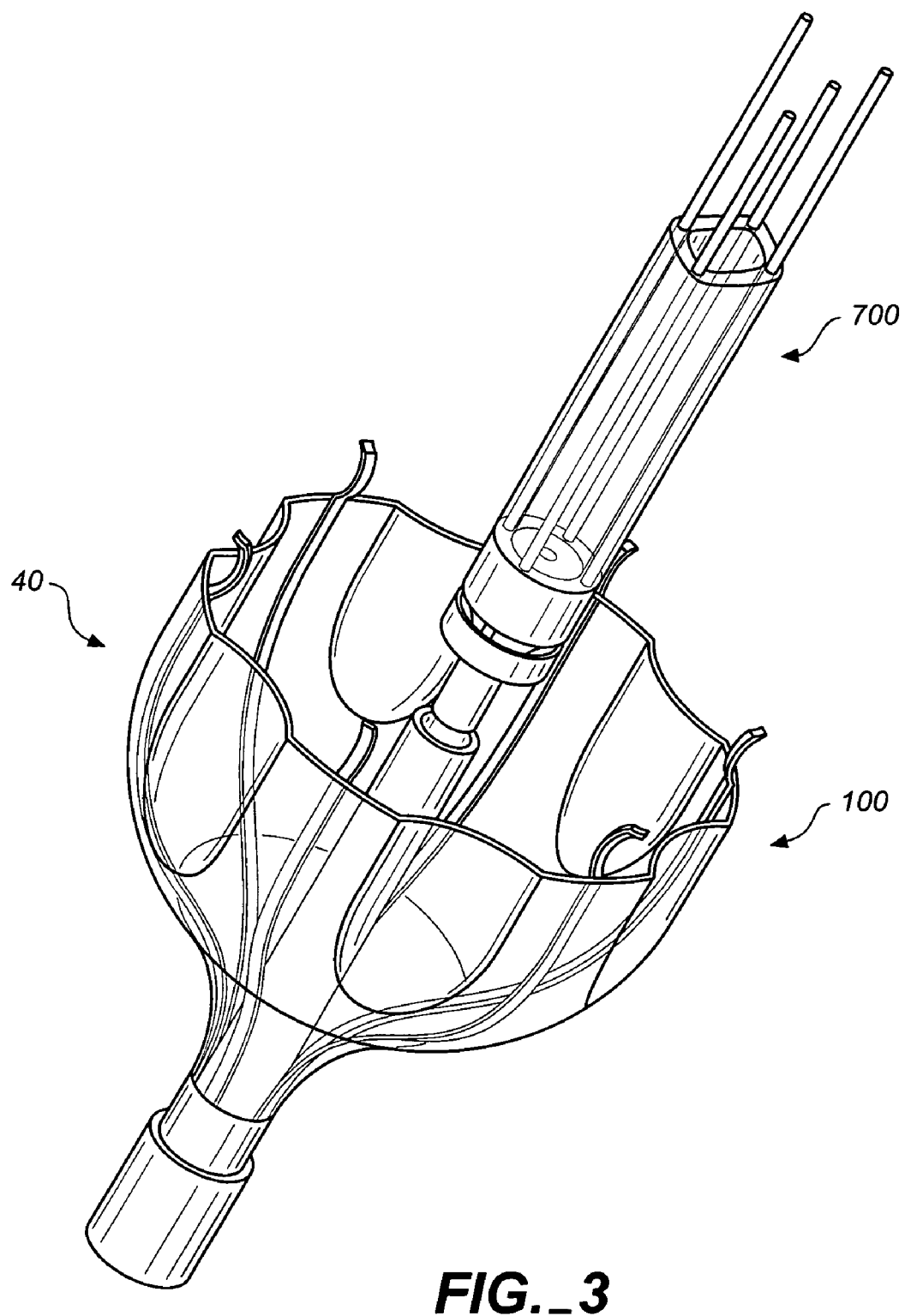
FIG._3

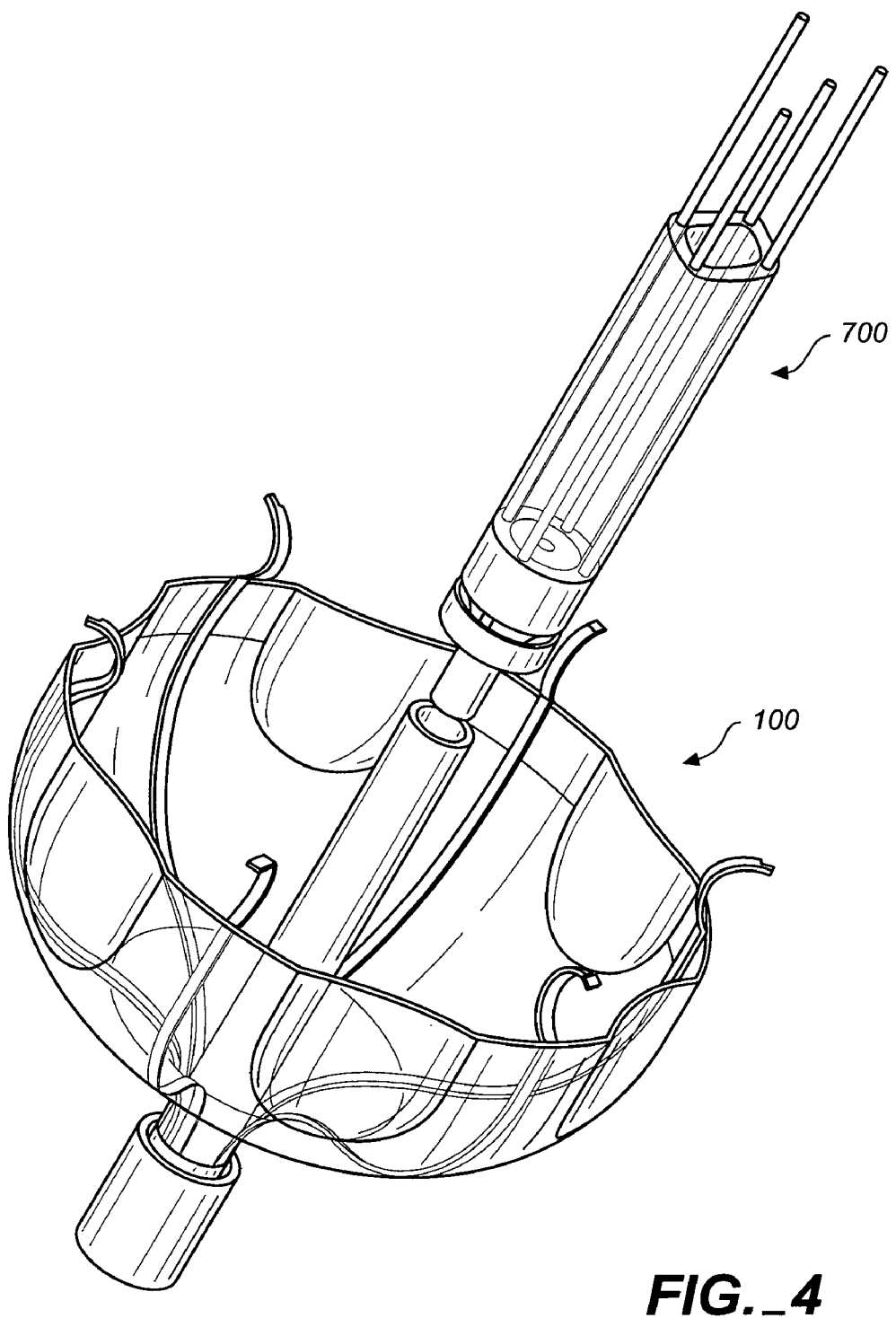
FIG._4

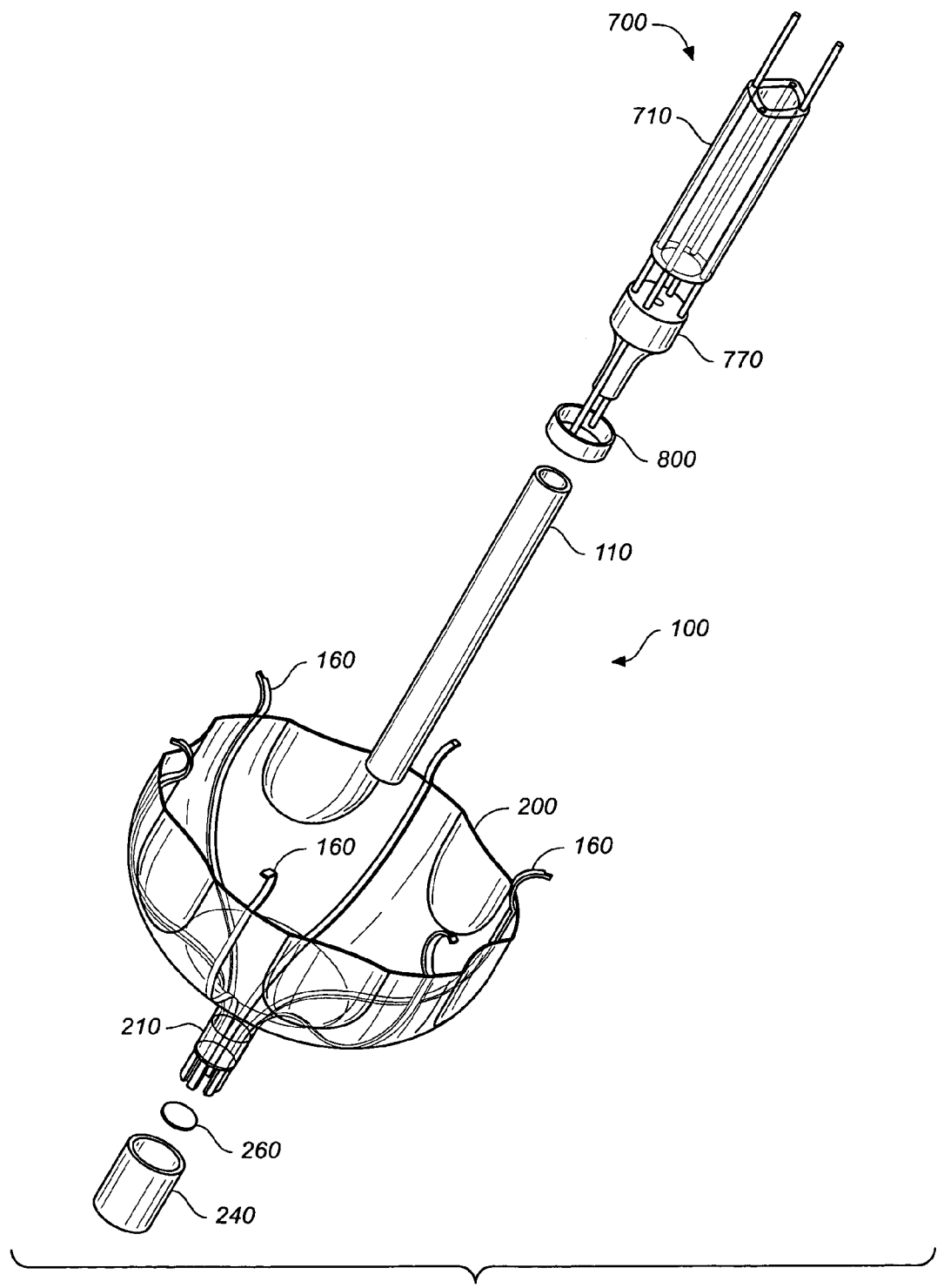
FIG._5

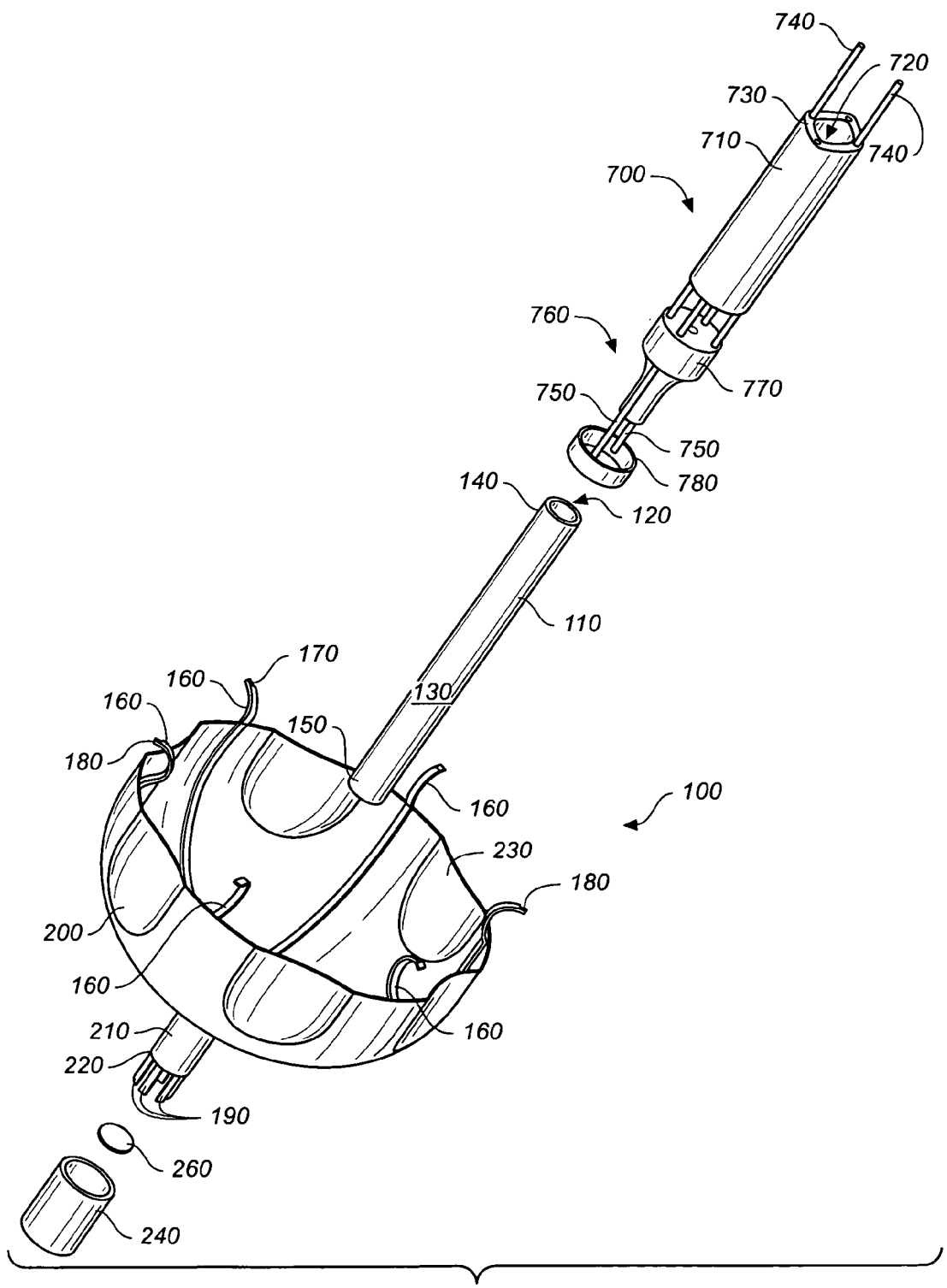
FIG._6

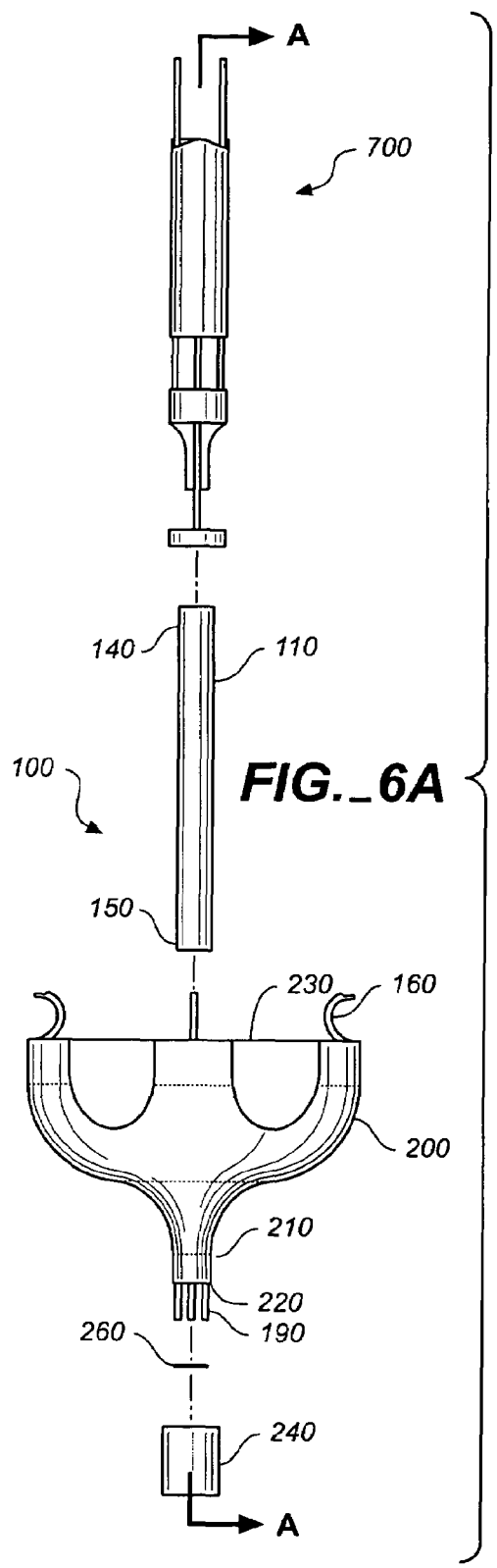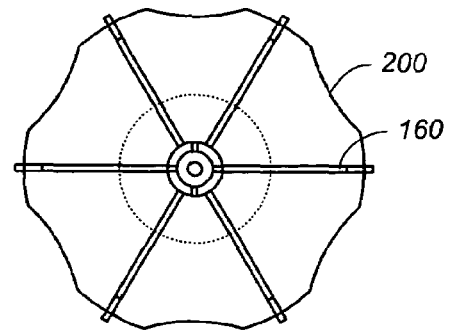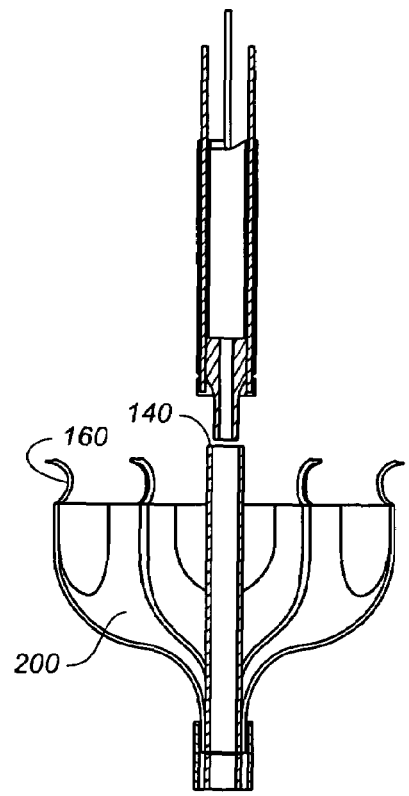

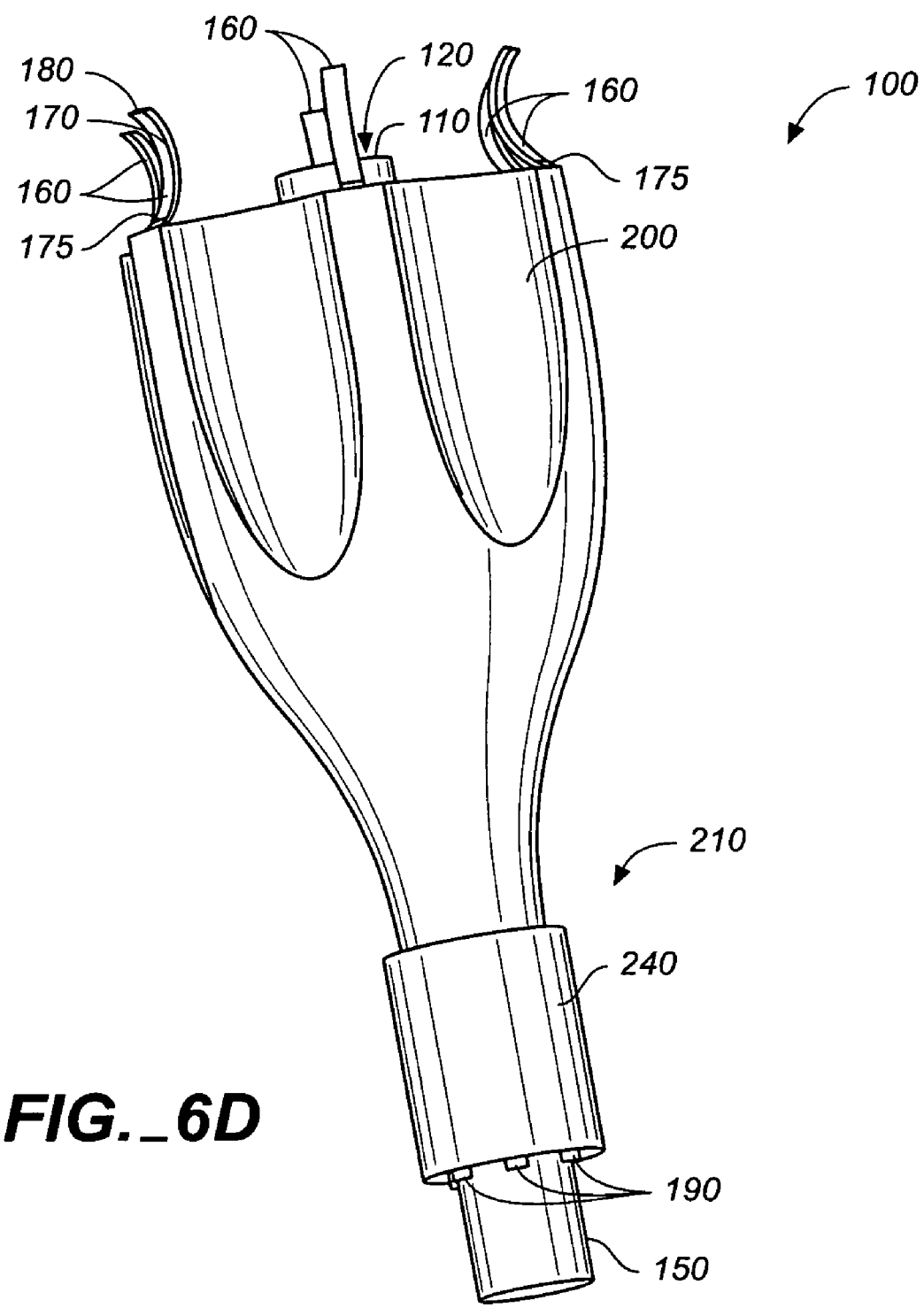
FIG._6D

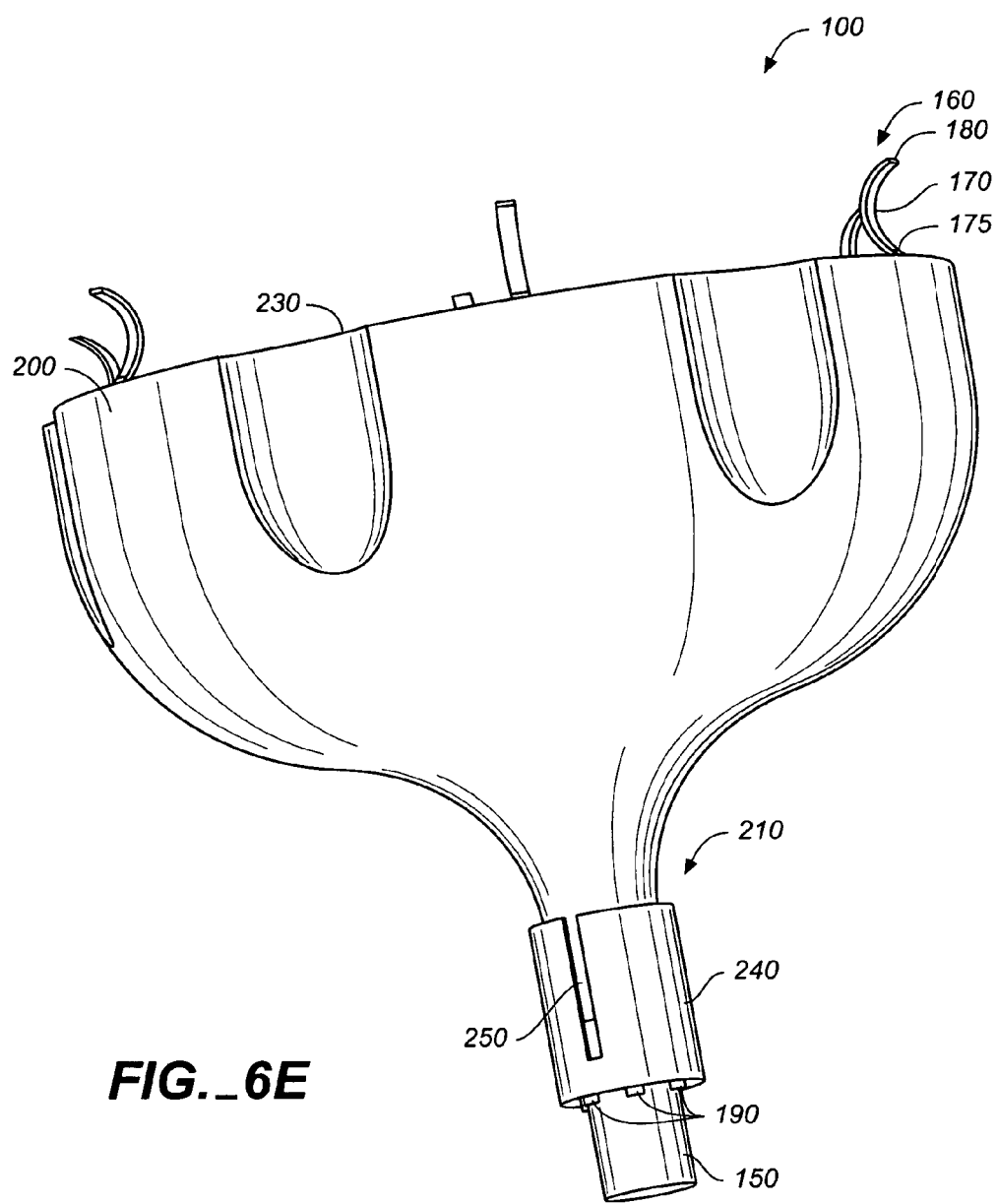
FIG._6E

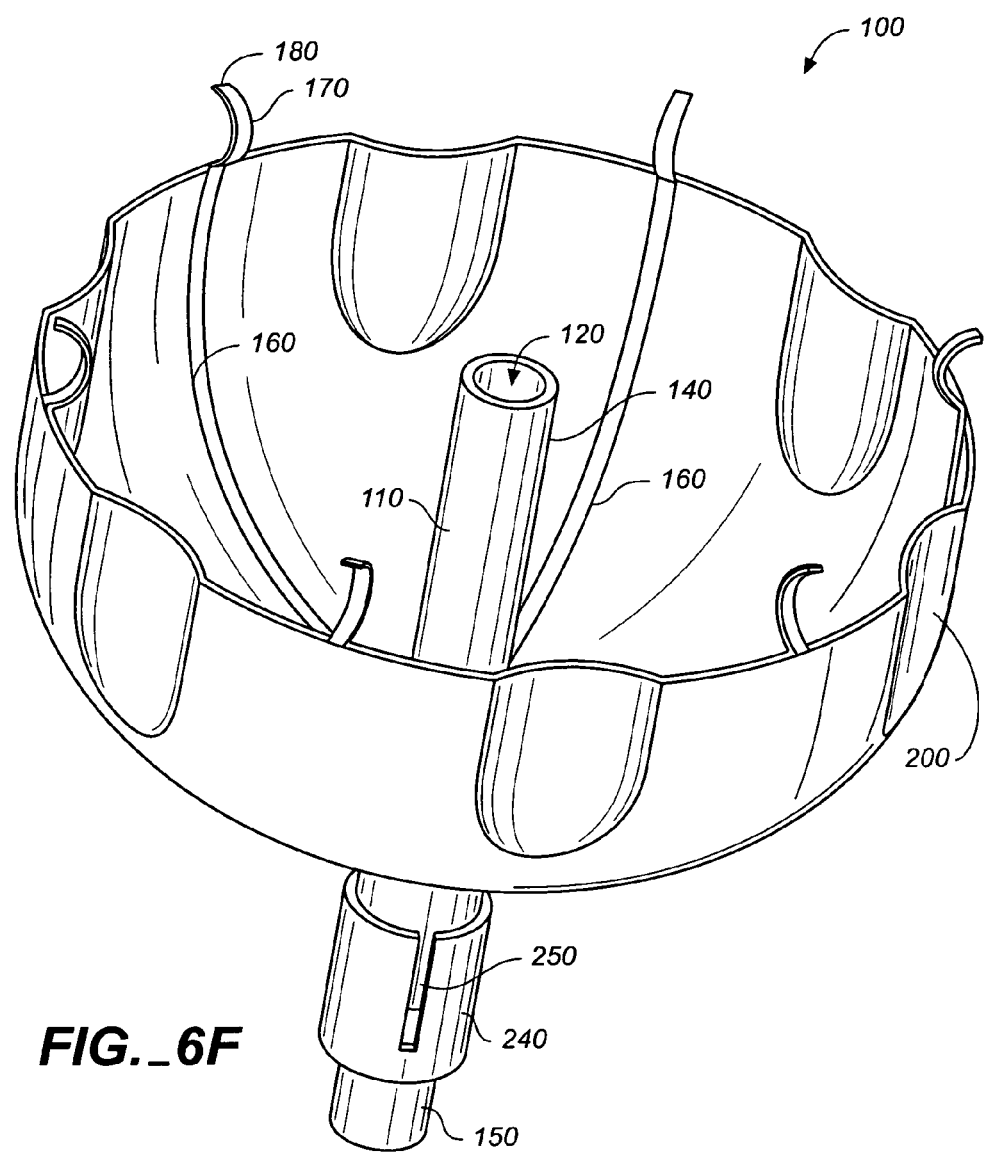
FIG._6F

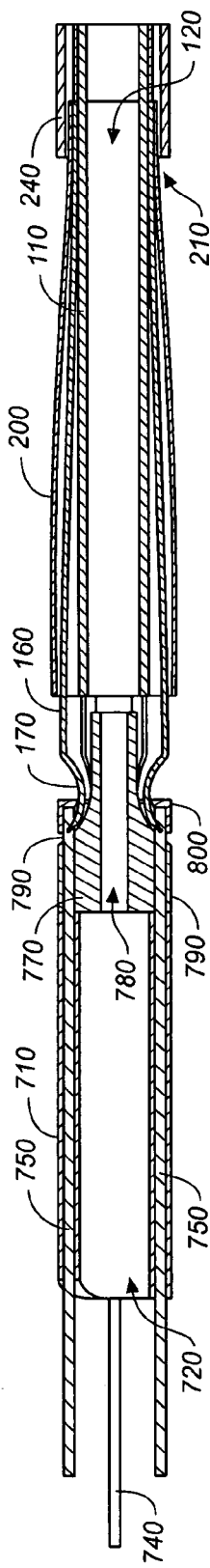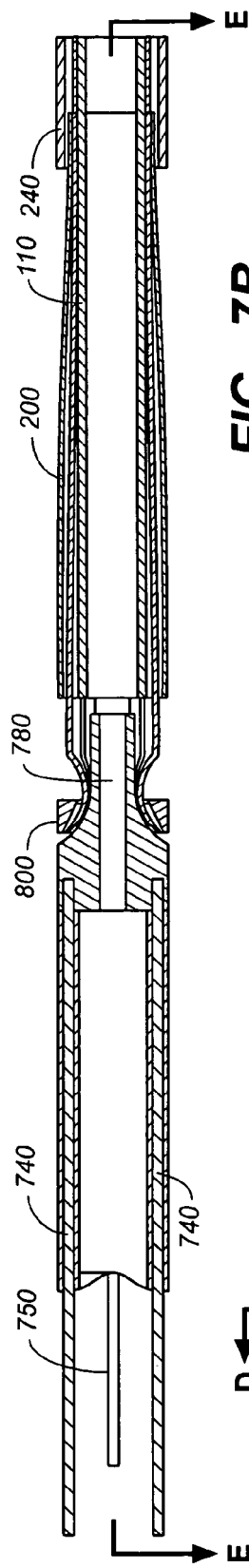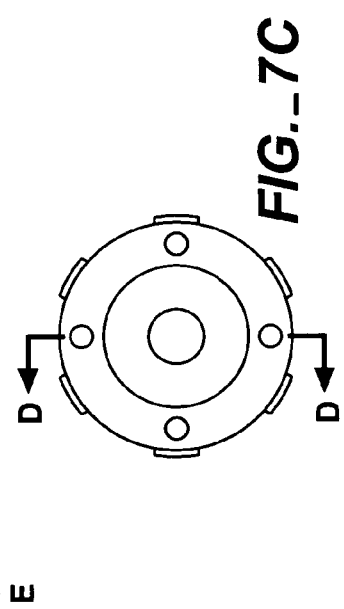

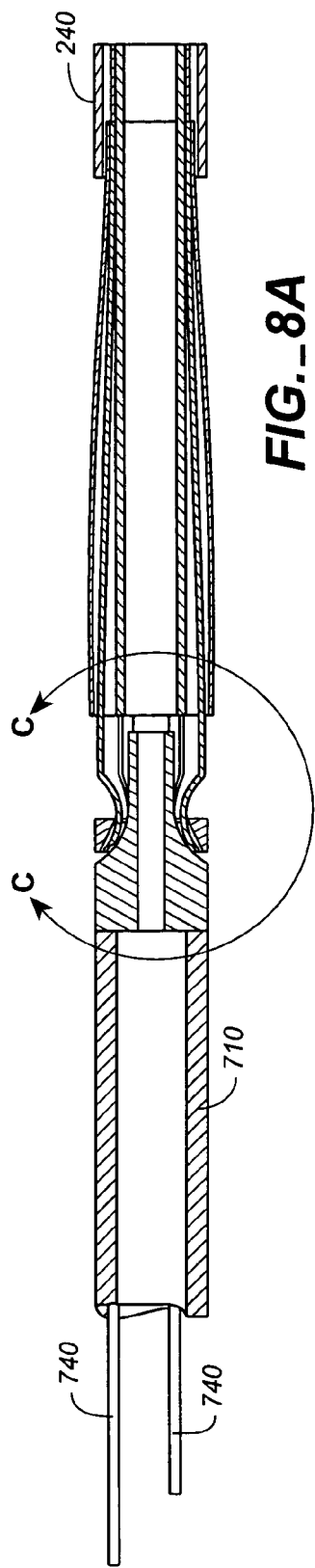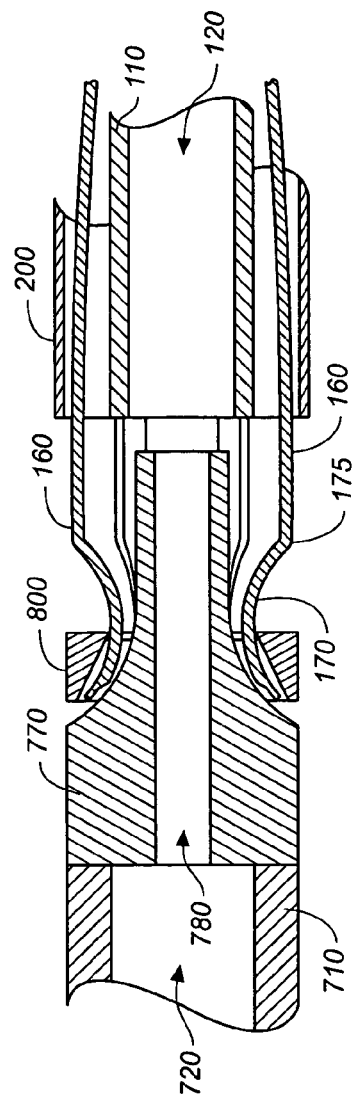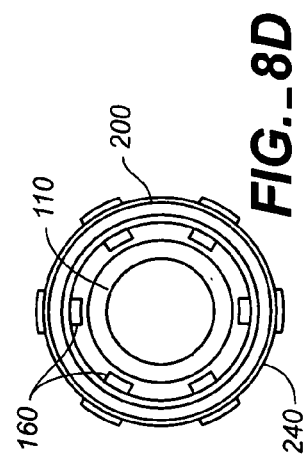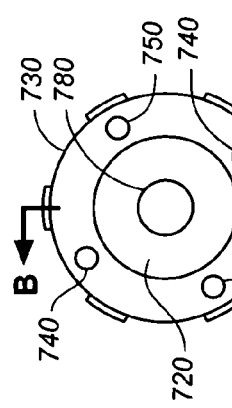
FIG._8A
FIG._8C
FIG._8B
FIG._8D

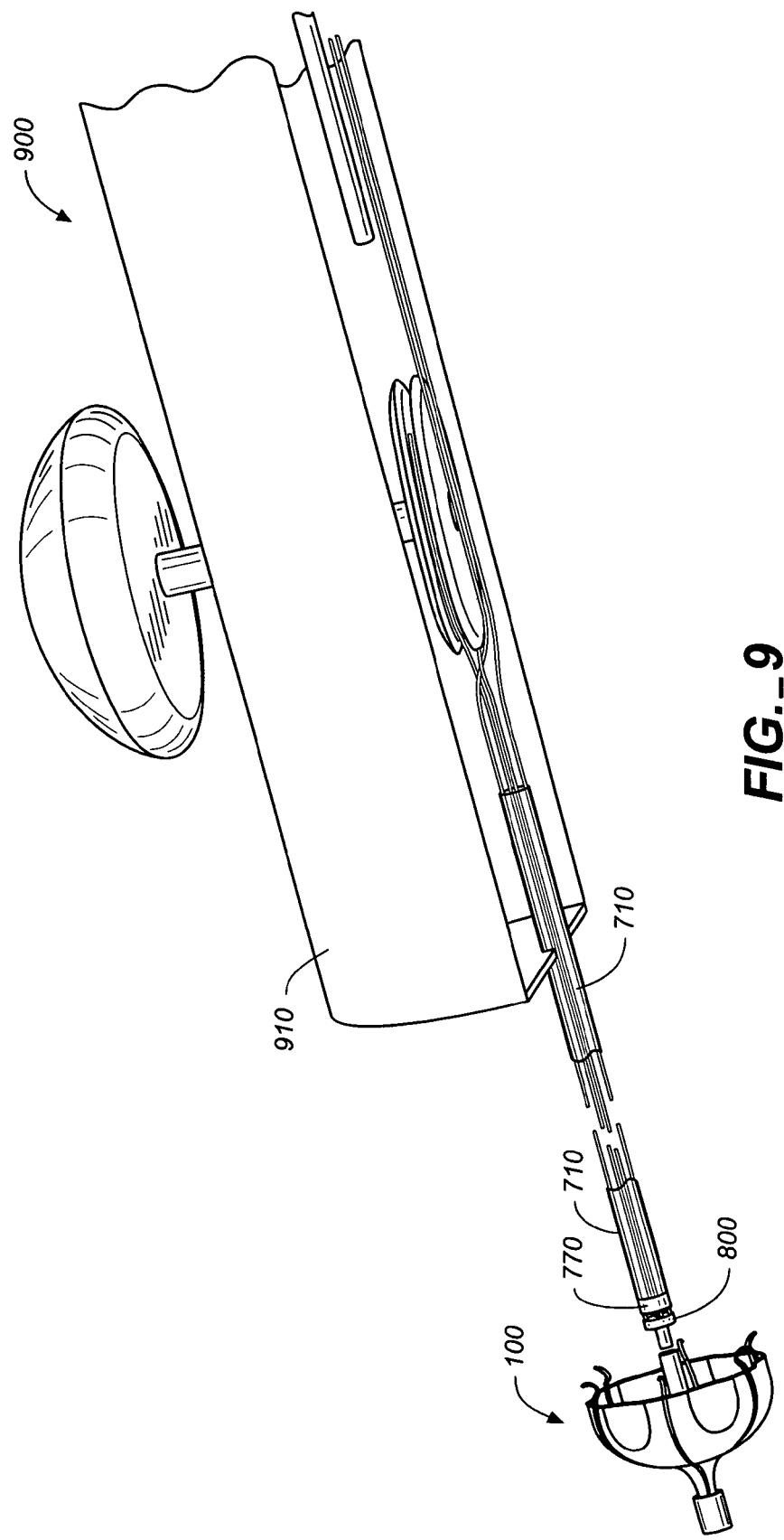
FIG._9

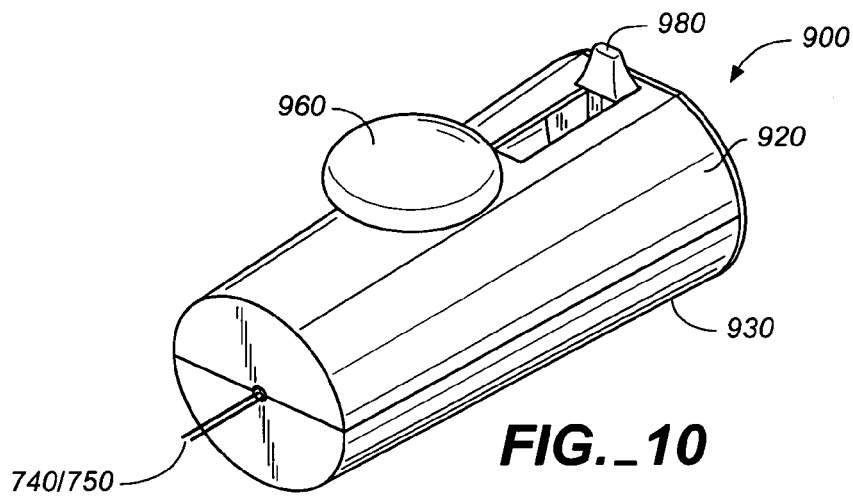
FIG._10
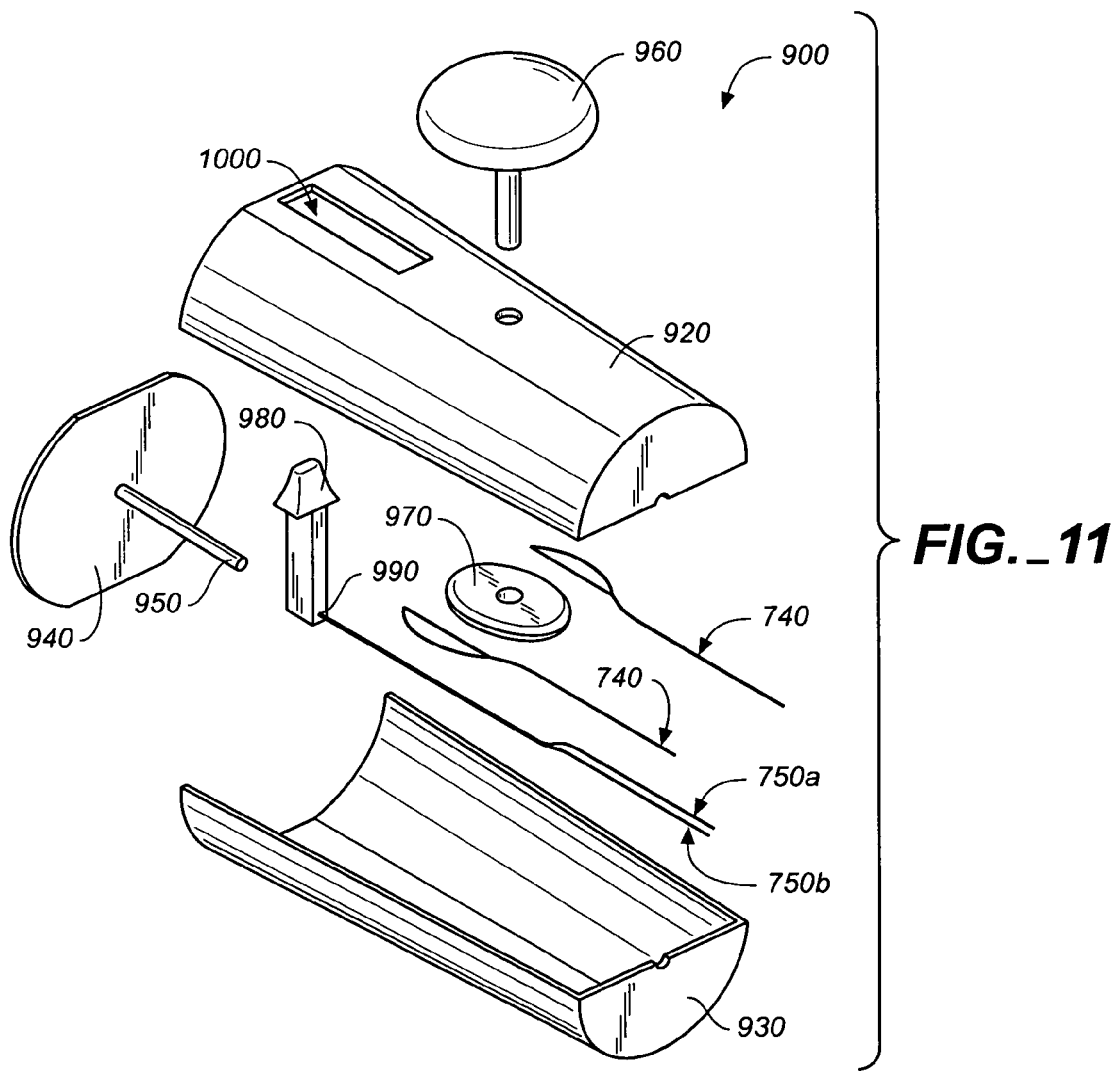
FIG._11

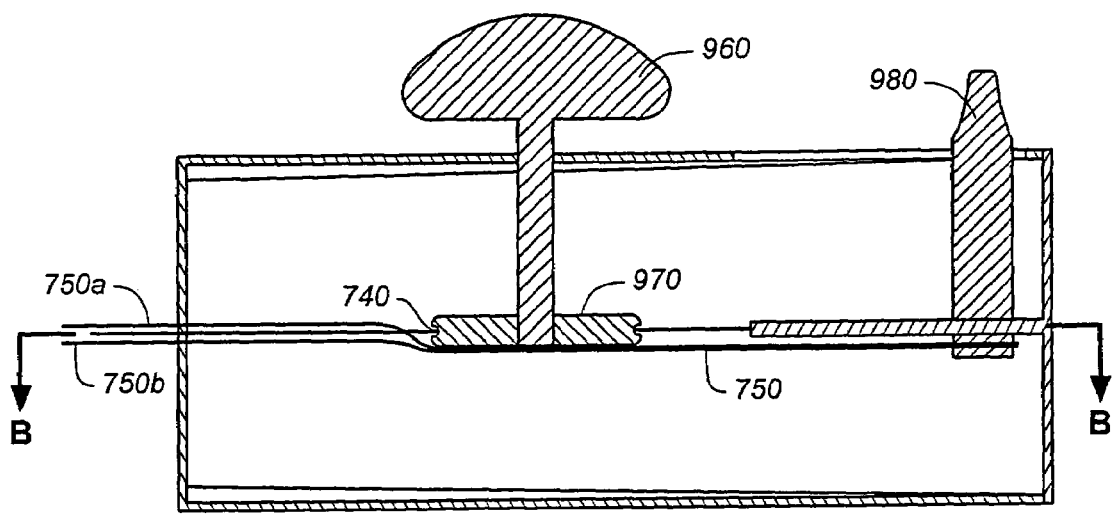
FIG._12A
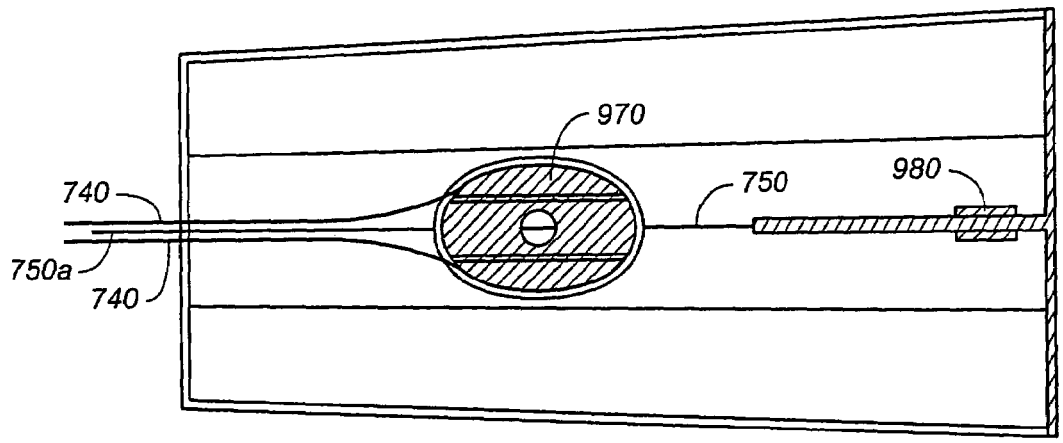
FIG._12B
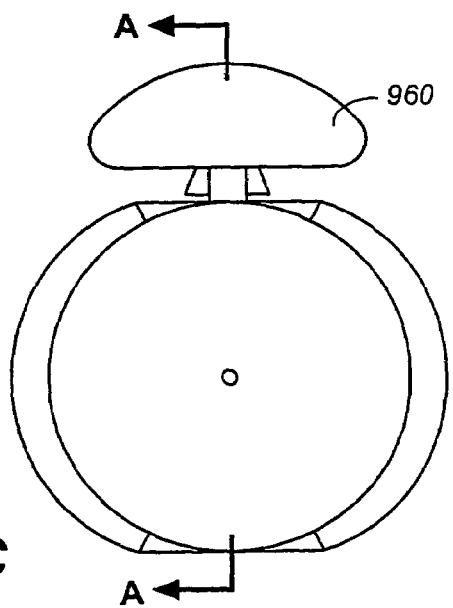
FIG._12C

INTRA-BRONCHIAL APPARATUS FOR ASPIRATION AND INSUFFLATION OF LUNG REGIONS DISTAL TO PLACEMENT OR CROSS COMMUNICATION AND DEPLOYMENT AND PLACEMENT SYSTEM THEREFOR

CROSS REFERENCE TO RELATED APPLICATIONS

The present application claims the benefit of the filing date of U.S. Provisional Patent Application, Ser. No. 60/629,451, filed Nov. 18, 2004.

STATEMENT REGARDING FEDERALLY SPONSORED RESEARCH OR DEVELOPMENT

Not applicable.

REFERENCE TO A MICROFICHE APPENDIX

Not applicable.

TECHNICAL FELD

The present invention relates generally to a method and apparatus for treatment of certain pulmonary diseases, more particularly to a bronchial obstruction apparatus, which may be either a plug or a uni-or bi-directional valve, and a deployment and placement system adapted for the novel apparatus. Still more particularly, the present invention is an intra-bronchial apparatus for the aspiration and/or insufflation of lung regions distal to placement of the apparatus and to cross-communication from other airways to other lung regions. The inventive apparatus is particularly well-adapted for the delivery of pharmacological agents and/or for the collapse or partial collapse of lung regions to restrict or reduce effective lung volume for the treatment of Chronic Obstructive Pulmonary Disease (COPD).

BACKGROUND INFORMATION AND DISCUSSION OF RELATED ART

COPD is characterized by airflow obstruction due to chronic bronchitis or emphysema. It a progressive disease with no known cure. Preferred treatment modalities include the adoption of healthy living habits to prevent further respiratory damage, pharmacotherapy, and surgery. The first improves the quality of life of the patient but is insufficient to reverse the course of the disease and does not provide relief in the long-term. The second, pharmacotherapy, is largely palliative, and no studies support even the proposition that even early drug intervention can significantly alter the course of COPD. And the third, surgery (i.e., lung volume reduction surgery, or LVRS), carries with it several risks even apart from those that attend any complicated thoracic surgery, though it is admittedly known to provide improvements in forced expiratory volume, a decreased total lung capacity, and improvement in lung function.

Improvements deriving from LVRS have led researchers to explore non-surgical methods of reducing total lung volume. The most well accepted approach has been to provide means of obstructing an airway to selected region or regions of the lungs to collapse a portion of a lung. The efficacy of an obstruction may be enhanced if it is placed permanently or semi-permanently.

Patents relating to methods and apparatus for such a procedure include: U.S. Pat. No. 6,258,100, to Alferness, et al, which discloses a method of collapsing a lung region by placing in an air passageway a plug which prevents air flow in both directions or a one-way valve which permits exhaled air to pass but precludes inhaled air from passing. The method shows the steps of inserting a conduit into the air passageway communicating with the lung portion to be collapsed; advancing an obstruction device down the conduit into the air passageway; deploying the obstruction device, thereby sealing the air passageway and causing it to collapse.

A second patent to Alferness, et al., namely, U.S. Pat. No. 6,293,951, shows a method and apparatus similar to that disclosed in the '100 patent, but further including a method and apparatus for pulling a vacuum within the lung portion for first collapsing the lung portion, and then, while the lung portion is collapsed, placing and deploying an obstruction device to maintain the lung portion in a permanently collapsed state.

U.S. Pat. No. 6,632,243, to Zadno-Azizi et al, teaches a method and apparatus for body fluid flow control in urinary, venous or pulmonic ducts or passageways. It includes the ability to seal about the device in the fluid passageway, a placement and retention format for the device, and a valve body capable of either or both a pressure threshold for operation and a one-way flow restriction. The valve body preferably has end bulk resilience and a passage through the valve body which is closed by that bulk resilience. One-way flow is produced by a flap or other inhibitor physically impeding flow in one direction or by a configuration of the valve to employ passage pressure to prevent opening.

U.S. Pat. No. 6,592,594, to Rimbaugh et al., discloses a method and apparatus for deploying a bronchial obstruction device in an air passageway, the system including a conduit configured for insertion into and down the trachea, into a bronchus communicating with the trachea, and then into the air passageway communicating with the lung portion. The system includes a capsule dimensioned to house the bronchial obstruction device and to be advanced down an internal lumen of the conduit into the air passageway. The capsule has a break-away distal end configured to release the bronchial obstruction device for deployment in the air passageway upon being pushed from the capsule by a pusher member.

U.S. Pat. No. 6,328,689, to Gonzalez, et al., teaches a lung constriction device, including a sleeve of elastic material, configured to cover at least a portion of a lung. The sleeve has a pair of opened ends to permit the lung portion to be drawn into the sleeve. Once drawn therein, the lung portion is constricted by the sleeve to provide air leak suppression and to reduce the size of the lung portion.

U.S. Pat. No. 6,679,264, to Deem et al., shows methods and apparatus for placing and deploying an air flow control element having a valve to prevent airflow in the inhalation direction but permit airflow in the exhalation direction. The flow control element is guided to and positioned at the site by a bronchoscope introduced into the patient's trachea and used to view the lungs during delivery of the flow control element. The valve may include one, two or more valve elements, and it may be collapsible for easier delivery. A source of vacuum or suction may be used to increase the amount of fluid withdrawn from the lung tissue.

U.S. Pat. Appl. No. 2003/0070682, to Wilson et al, teaches methods and devices for regulating fluid flow to and from a region of a patient's lung to achieve a desired fluid flow dynamic to a lung region during respiration and/or to induce collapse in one or more lung regions. A flow control device is implanted into a bronchial passageway. The flow control device includes a valve to regulate fluid flow, a seal partially surrounding the valve, and an anchor secured to the seal. The anchor exerts a radial force against an interior wall of the bronchial passageway to retain the flow control device in a fixed location in the bronchial passageway. The flow control device can either eliminate air flow into the targeted lung region or it can permit a regulated airflow to and from the targeted lung region to achieve an improved air flow dynamic that does not result in lung collapse. A delivery system is also disclosed. It includes a catheter having a proximal end and a distal end, and it is sized for insertion into a respiratory tract and deployed to a target location of a bronchial passageway through a trachea. A housing near the distal end of the catheter has an interior cavity that partially receives the flow control device. An ejection member is movably positioned in the housing and is mechanically coupled to an actuation device so that the flow control device can be ejected out of the housing.

U.S. Pat. No. 6,712,812, to Roschak et al, teaches for altering gaseous flow within a lung. The devices produce collateral openings or channels through the airway wall so that oxygen depleted/carbon dioxide rich air is able to pass directly out of the lung tissue to facilitate both the exchange of oxygen ultimately into the blood and/or to decompress hyperinflated lungs.

Several more recent patents and/or patent applications disclose intra-bronchial valve devices and removable lung volume reduction devices. An especially prolific group collaborating in a very focused inventive enterprise for Spiration, Inc., of Seattle, Wash., have produced a series of interesting applications, notable among them: US Pat. Appl. Ser. Nos. 2003/0181922; US Pat. Appl. Ser. No. 2003/0195385; US Pat. Appl. Ser. No. 2003/0216769; US Pat. App. Ser. No. 2004/0143282; US Pat. Appl. Ser. No. 2004/0167636; US Pat. Appl. Ser. No. 2004/0243140; US Pat. Appl. Ser. No. 2005/0033310; and US Pat. Appl. Ser. No. 2005/0033344. While difficult to generalize about a large body of art, the foregoing collection all relate to removable anchored lung volume reduction devices employed and methods for using the devices.

The foregoing patents reflect the current state of the art of which the present inventor is aware. Reference to, and discussion of, these patents is intended to aid in discharging Applicant's acknowledged duty of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

BRIEF SUMMARY OF THE INVENTION

In its most essential aspect, the present invention is a selectively anchored intra-bronchial apparatus for placement and deployment into selected airways. When deployed, the apparatus creates a restriction of air flow to one or more targeted lung regions and achieves total lung volume reduction through a collapse or partial collapse of the targeted regions. The inventive apparatus includes an air flow valve having a through lumen that facilitates selective drug delivery concurrent with a lung volume reduction procedure. A novel specialized placement and deployment system may be employed and is also disclosed herein.

The intra-bronchial apparatus of the present invention is a restrictive air flow control element that may be either an air passageway plug or one-way or two-way valve (and for purposes of brevity, the intra-bronchial apparatus is synonymously referred to herein as the "air flow control valve" or more simply the "valve"). In its most essential aspect, the valve comprises a dynamic frame structure covered by a membrane. It has a collapsed and a deployed configuration, and an infinite range of configurations between the deployed and collapsed configuration. When in its collapsed configuration, it is elongate and substantially cylindrical; when deployed, it expands outwardly under mechanical force to assume a parachute-like configuration.

Structurally, the air flow control valve comprises a valve frame including a center tube, a plurality of spaced-apart, arcuate strut arms radially disposed at their lower ends around the outer diameter of the center tube and extending upwardly therefrom. A membrane is wrapped around and adhesively bonded, over coated, or woven at its lower portion to the lower end of the center tube and strut arms. The lower portion of this assembly is then inserted into a collet to form a press fit. The collet may include one or more longitudinal slits to facilitate press fit affixation at the lower end of the center tube and struts. When assembled, the lower portion of the valve assembly urges the upper portion of the struts outwardly from the longitudinal axis of the apparatus, and this outward force is restrained and retained by structure in the deployment and placement apparatus during deployment. When not restrained, the strut arms are urged naturally into a deployed configuration that pulls the membrane into an open form, much like an open parachute.

The membrane is borne by and wrapped around the strut arms and the center tube such that a portion of the strut arms projects upwardly beyond the upper rim of the membrane to provide anchoring structure at the tips of the arms. At the tips, the struts have at least one point adapted for contact with the interior wall of an air passageway inner lumen. The membrane is made from a metallic or polymeric material that provides an air flow restriction while simultaneously providing access to a central lumen that facilitates the delivery of medications to the lung region addressed through the center lumen of the valve. In this manner, while a lung region is collapsed or partially collapsed, bacteria and viral infections in lung tissue distal to the intra-bronchial valve may be treated.

As noted, the membrane may be attached to the frame elements by means of molding, adhesive bonding, weaving or energy fusion (e.g., melting the membrane onto the frame.) The frame member itself can be assembled and mechanically press fit as a discrete structure, or its elements may be assembled by spot fusion or with spot adhesives to tack and secure the frame for a long fatigue life. It may be fabricated from a shape memory material charged with alpha radiation to deliver therapeutic radiation to specific sites where cancerous or other pathological neoplastic processes are occurring.

The center tube may include a lumen, in which event the anchor linkage is mated to the center tube by fusion, adhesion or press fit, which ensures that the central opening through the lumen is not compromised. The center tube lumen also provides access for an aspiration or insufflation port to correct the air or fluid in the lung region distal to the valve placement. The action to affect the lung region can occur by auxiliary devices (such as a plug or inner membrane with openings tailored to the air flow requirements) or by the implementation of a system complementing the intra-bronchial device utilizing MEMS or NANO technologies. Such a mechanical device might assist in the exhalation of air distal to the device placement. The NANO or MEMS system may communicate to an external control system via wire, thread or wireless transmitter to provide information on valve system performance and effect. In addition, the center lumen may include a plug created from a pharmacological material to allow elution to the proximal or distal area of the lung.

For placement and deployment, the strut arms can be compressed against the center tube such that the valve frame is collapsed into a small diameter shape. When deployed in an air passageway, the strut arms apply an outward radial force that stabilizes the frame in the airway. The membrane then provides air flow restriction in the air way such that air shall cannot travel past the membrane unless a passageway is left open through the center of the valve frame through the central tube and the collet.

Also disclosed is a method and apparatus for deploying and placing the intra-bronchial apparatus in an air passageway, such as a mainstem bronchus or a bronchial branch or sub-branch. The system comprises a deployment catheter having a distal end adapted for connection to the intra-bronchial valve described in the foregoing paragraphs and a proximal end operatively coupled to a handle and control assembly. The catheter includes a center lumen that provides access from the proximal end to the distal tip and facilitates use of auxiliary devices, such as a bronchoscope, and further allows for access to and through the valve to manipulate the valve, treat or deliver drugs to the lung regions distal to the valve, or provide wire access for delivery of an over-the-wire device, such as those employed in cardiovascular systems. A side port may be added proximate the distal tip and the proximal tip to provide a secondary access.

The deployment catheter includes four lumen extending the length of the catheter and enclosed between the interior and exterior walls of the catheter body. Within these lumen four wires are slidably inserted, two for control during steering operations, and two for control of the obstruction device release mechanism. The proximal end of the deployment catheter is coupled to a handle assembly having steering control means and a release control handle that allows for the selective release of the obstruction device.

The method of utilizing the present invention comprises specifying and identifying a target location in an air passageway in which the intra-bronchial apparatus will be deployed; providing the disclosed deployment and placement device having steering means and intra-bronchial apparatus attachment and selective release means. The intra-bronchial apparatus is connected to the distal end of a catheter of the deployment and placement device. The method steps further include positioning the intra-bronchial apparatus within the air passageway so that it is positioned at the target location; and detaching the intra-bronchial apparatus from the deployment device. When so deployed, drugs for treating pulmonary conditions can be selectively delivered through the central lumen of the valve member center tube.

Other novel features which are characteristic of the invention, as to organization and method of operation, together with further objects and advantages thereof will be better understood from the following description considered in connection with the accompanying drawing, in which preferred embodiments of the invention are illustrated by way of example. It is to be expressly understood, however, that the drawing is for illustration and description only and is not intended as a definition of the limits of the invention. The various features of novelty which characterize the invention are pointed out with particularity in the claims annexed to and forming part of this disclosure. The invention resides not in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the Abstract is to enable the national patent office(s) and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of this application, which is measured by the claims, nor is it intended to be limiting as to the scope of the invention in any way.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

BRIEF DESCRIPTION OF THE SEVERAL
VIEWS OF THE DRAWINGS

The invention will be better understood and objects other than those set forth above will become apparent when consideration is given to the following detailed description thereof. Such description makes reference to the annexed drawings wherein:

FIG. 1 is an upper perspective view of the intra-bronchial apparatus of the present invention, shown in its collapsed configuration and attached at its upper end to the distal end of a placement and deployment device;

FIG. 2 is an upper perspective view of the apparatus of FIG. 1, shown in a partly collapsed configuration shortly after released from a placement and deployment device, FIG. 3 is an upper perspective view of the inventive apparatus, again shown in a partly collapsed configuration, but approaching full deployment;

FIG. 4 is an upper perspective view showing the inventive apparatus in a fully deployed configuration;

FIGS. 5 and 6 are exploded upper perspective views showing the primary structural elements of the intra-bronchial apparatus and the distal portion of the deployment and placement system of the present invention;

FIG. 6A is an exploded side view in elevation showing the primary structural elements of the inventive apparatus and the distal portion of the deployment system;

FIG. 6B is a cross-sectional side view in elevation taken along Section lines A-A of FIG. 6A;

FIG. 6C is a top plan view of the intra-bronchial apparatus with a cross-sectional view of the distal portion of the deployment and placement apparatus;

FIG. 6D is a lower perspective view of the inventive intra-bronchial apparatus in a partially collapsed configuration, while FIG. 6E is the same view showing the apparatus in the fully deployed configuration;

FIG. 6F is an upper perspective view of the inventive intra-bronchial apparatus in a fully deployed configuration;

FIG. 7A is a cross-sectional side view in elevation of the inventive intra-bronchial apparatus attached to the distal portion of the inventive deployment and placement system, taken along Section lines E-E of FIG. 7B;

FIG. 7B is a cross-sectional side view in elevation of the apparatus of FIG. 7A taken along Section lines D-D of FIG. 7C;

FIG. 7C is a cross-sectional top plan view of the apparatus of FIGS. 7A-B;

FIG. 8A is a cross-sectional side view in elevation of the inventive intra-bronchial apparatus attached to the distal portion of the inventive deployment and placement system, taken along Section lines B-B of FIG. 8B;

FIG. 8B is a cross-sectional top plan view of the distal portion of the deployment and placement system and intra-bronchial apparatus of FIG. 8A;

FIG. 8C is a detailed cross-sectional side view in elevation taken along detailed portion indicated in FIG. 8A;

FIG. 8D is a bottom plan view of the apparatus of FIGS. 8A-C;

FIG. 9 is a lower perspective view showing the proximal handle assembly portion of the novel deployment and placement system, here shown releasing the intra-bronchial apparatus of the present invention;

FIG. 10 is a perspective view of the proximal handle assembly of the deployment and placement system of the present invention;

FIG. 11 is an exploded view of the apparatus of FIG. 10;

FIG. 12A is a cross-sectional side view in elevation of the apparatus of FIGS. 10 and 11, taken along Section lines A-A of FIG. 12C;

FIG. 12B is a cross-sectional top plan view of the apparatus of FIG. 12A, taken along Sections lines B-B of FIG. 12A; and FIG. 12C is a distal end view of the apparatus of FIGS. 12A and 12B.

DRAWING REFERENCE NUMERAL LEGEND 100 air flow control valve
700 deployment and placement system device
110 center tube
120 central lumen of center tube
130 outside surface of center tube
140 upper portion of center tube
150 lower portion of center tube
160 arcuate strut arms
170 upper arcuate portions of arcuate strut arms
175 lower end of upper arcuate portion of strut arms
180 tips of strut arms
190 lower ends of strut arms
200 air restriction membrane affixed to strut arms and center tube
210 tubular portion of air restriction membrane around the lower portion of the center tube and lower ends of strut arms
220 lower border of membrane
230 upper border of membrane
240 collet over the tubular portion of membrane/center tube/strut arm assembly
250 longitudinal slits in collet
260 inner membrane 700 deployment and placement system for air flow control valve
710 deployment and placement catheter
720 center lumen of deployment and placement catheter
730 body portion encasing and defining center lumen
733 outside diameter of catheter
736 control wire lumen
740 steering wires
750 release ring wires
760 distal end of catheter
770 steering tip
780 center lumen of steering tip
790 throughholes in steering tip
800 release ring
900 steering and release handle assembly
910 housing for steering and release handle assembly
920 upper portion of housing
930 lower portion of housing
940 back plate
950 stem
960 steering knob
970 steering wire cam
980 release ring lock handle
990 through hole
1000 slot through which lock handle extends

DETAILED DESCRIPTION OF THE INVENTION

Referring to FIGS. 1 through 12C, wherein like reference numerals refer to like components in the various views, there is illustrated a new and improved intra-bronchial apparatus for aspiration or insufflation of lung regions distal to the apparatus placement or air passageway cross-communication. The air flow control valve portion apparatus is generally denominated 100 herein, while the deployment and placement system device is generally denominated 700.

FIGS. 1-8D illustrate a first preferred embodiment of the air flow control valve portion of the present invention. These views collectively show that the valve comprises a center tube 110 having a central lumen 120, an outside surface 130, an upper portion 140, and a lower portion 150. The valve further includes a plurality of resilient, arcuate strut arms 160, each having an upper arcuate portion 170 with a tip 180 shaped for anchoring the valve on the interior lumen wall of a body cavity, duct, vessel, or passageway. The lower ends 190 of the strut arms are disposed in an evenly spaced arrangement around the lower portion 150 of the center tube 110.

A woven or polymeric air restriction membrane 200 is molded, adhesively bonded, woven, or fused to the strut arms and center tube to form a columnar or tubular portion 210 around the lower portion of the center tube and lower ends 190 of the strut arms. The membrane has a lower border 220 and an upper border 230, the latter encircling the strut arms immediately under the lower end 175 of the upper arcuate portion of the strut arms.

A collet or ferrule 240 is placed over the tubular portion 210 of the air restriction membrane/center tube/strut arm assembly. The collet may include one or more longitudinal slits 250 to facilitate a firm press-fit placement.

Optionally, the valve may include an inner membrane 260 disposed inside the central lumen of the center tube, which may be either a solid disc that permits no passage or leak of gases in or out, or it may be provided with slits or flaps or other valve elements that permit one-way or bi-directional passage of air, as is known in the art. The inner membrane cooperates with the patient's natural mucous production to create a seal. The valve may be introduced into the air passageway with the inner membrane fully intact and impermeable and thereafter perforated by medical instrument for treatment of the lung region distal to the device.

FIGS. 1-5 and 7A-9 show both the air flow control element of the present invention, as well as the distal portion of the catheter of the deployment and placement system 700 of the present invention. The deployment and placement catheter 710 includes a center lumen 720 extending the entire length of the catheter and a body portion 730 encasing and defining the center lumen 720. Disposed between the center lumen and the outside diameter 733 of the catheter are at least four control wire lumen 736 in which at least two steering wires 740 are slidingly disposed, and at least two release ring wires 750 are also slidingly disposed.

At the distal end 760 of the catheter is a steering tip 770 operatively connected to steering wires 740. The tip includes a center lumen 780 coaxial with the catheter's center lumen. The steering tip includes two throughholes 790 so that the release ring wires 750 fasten at their ends to a release ring 800.

FIGS. 9-12C show the handle assembly and control elements of the deployment and placement device of the present invention. These views collectively show that the deployment and placement catheter 710 connects the air flow control element with a steering and release handle assembly 900, which includes a housing 910 having upper and lower portions 920, 930, and a back plate 940 having a stem 950. A steering knob 960 is disposed in the upper portion and is connected to a steering wire cam 970, around which are fastened the proximal ends of the steering wires 740. Control inputs through the steering knob exert right or left pulling forces communicated the entire length of the steering wire and catheter to the steering tip disposed at the distal end of the catheter.

A release ring lock handle 980 includes a throughhole 990 into which stem 950 is inserted, and along which the lock handle moves longitudinally. The handle extends upwardly through a slot 1000 in the upper portion 920 of the housing for forward and backward control inputs by the user. The handle is connected to top and bottom release ring wires, 750a, 750b, which extend the length of the deployment catheter 710 to the release ring 800.

Deployment proceeds as follows: When connected to the air flow control valve assembly, the steering tip at the distal end of the deployment and placement system catheter is inserted into the center lumen 120 of the center tube 110; the strut arms 170 are bent, gathered, and bunched at their upper arcuate ends 170 around the upper portion 140 of the center tube to bring the membrane 200 of the valve into a collapsed configuration 20 (FIGS. 1, 7A-B, 8A). The release ring is then disposed around the arcuate upper ends of the strut arms to retain and restrain them from moving outwardly, forced by their resilient characteristics and inherent shape memory. In this configuration, the assembly is adapted for insertion into a patient's trachea and steered into a target air passageway. When the target location is reached, the release ring is pulled off the strut arm upper ends by the operator controlling the release ring wires, thereby allowing the strut arms to move outwardly and urge the membrane into an open configuration. Increasingly, but partially open configurations 30, 40, are shown in FIGS. 2 and 3, while a fully open configuration 50, is shown in FIG. 4.

When directed to an air passageway and deployed therein, the tips of the strut arms are urged outwardly to engage the interior walls of the air passageway and to provide both a frictional fit and partial penetration of vessel tissue to resist displacement. While so deployed, the central lumen of the valve member center tube provides means for delivering drugs to treat pulmonary conditions concurrently with lung reduction therapy. The method comprises the steps of: (1) providing the above-describe intra-bronchial air flow restriction apparatus with the valve member with a central lumen; (2) deploying the intra-bronchial air flow restriction apparatus in an air passageway in fluid communication with a lung region to be collapsed and pharmaceutically treated; (3) anchoring the intra-bronchial air flow restriction apparatus in the air passageway wall; and (4) delivering therapeutic drugs to lung regions distal to the valve member through the central lumen of the valve member.

It will be appreciated by those with skill in the art that the present invention is unique in providing a restriction air valve with an accessible central lumen in substantially the center of the valve that allows selective delivery of drugs or other therapeutic actions in lung regions distal to the valve element.

The foregoing disclosure is sufficient to enable one having skill in the art to practice the invention without undue experimentation, and provides the best mode of practicing the invention presently contemplated by the inventor. While there is provided herein a full and complete disclosure of the preferred embodiments of this invention, it is not intended to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Accordingly, the proper scope of the present invention should be determined only by the broadest interpretation of the appended claims so as to encompass all such modifications as well as all relationships equivalent to those illustrated in the drawings and described in the specification.

What is claimed as invention is:

1. An intra-bronchial apparatus for deployment in a body cavity, duct, vessel, or air passageway to effect drug delivery concurrent with anchored placement of the intra-bronchial apparatus, said apparatus having a collapsed configuration and a deployed configuration, said apparatus comprising:

an air flow control valve having a center tube with a central lumen, an outside surface, an upper portion, a lower portion, and a plurality of spaced apart strut arms distributed around said outside surface of said lower portion of said center tube, said strut arms having a lower portion and an upper portion having tips for anchoring said valve on the interior wall of a body cavity, duct, vessel, or passageway when said intra-bronchial apparatus is in the deployed configuration;

an air restriction membrane having a portion attached to said strut arms and to said lower portion of said center tube to form a tubular portion around said power portion of said center tube and said lower ends of said strut arms;

an inner membrane disposed within the central lumen of said center tube, wherein when said intra-bronchial apparatus is in the deployed configuration in an air passageway, said inner membrane prevents the passage of gases while also permitting the selective delivery of drugs to lung tissue distal to the deployment site of said apparatus and wherein said outside surface of said upper portion of said center tube is spaced apart from said air restriction membrane; and a deployment and placement catheter, said deployment and placement catheter having a length from a distal end to a proximal end, and an outside diameter, and comprising a body portion encasing and defining a center lumen extending the entire length of said catheter; at least four control wire lumen disposed between the center lumen and said outside diameter of the catheter, including at least two steering wires each slidingly disposed in a lumen, and at least two release ring wires each slidingly disposed in a lumen; a steering tip disposed at said distal end of said catheter operatively connected to steering wires, said steering tip including a center lumen coaxial with the center lumen of said catheter, and having two throughholes through which the ends of said release ring wires are disposed; and a release ring attached to said release ring wires.

2. The apparatus of claim 1, further including a steering and release handle assembly connected to said apparatus through said deployment and placement catheter.

3. The apparatus of claim 2, wherein said steering and release handle assembly comprises:

a housing having a steering knob connected to said steering wires and said release ring wires.

4. The apparatus of claim 3, further including a release ring lock handle operatively connected to said release ring wires.

* * * * *